United States Patent [19]

Geke et al.

[11] Patent Number: 4,686,084
[45] Date of Patent: Aug. 11, 1987

[54] BENZOYL ALANINES AND THEIR USE AS CORROSION INHIBITORS

[75] Inventors: Juergen Geke, Duesseldorf; Josef Penninger, Hilden, both of Fed. Rep. of Germany

[73] Assignee: Henkel Kommanditgesellschaft auf Aktien, Duesseldorf, Fed. Rep. of Germany

[21] Appl. No.: 713,123

[22] Filed: Mar. 18, 1985

[30] Foreign Application Priority Data

Apr. 30, 1984 [DE] Fed. Rep. of Germany ....... 3416120

[51] Int. Cl.⁴ ............................................. C23F 11/12
[52] U.S. Cl. ..................................... 422/17; 252/390; 252/392; 252/394; 252/396; 422/14; 422/16
[58] Field of Search ............................ 422/14, 16, 17; 252/392, 394, 390, 396; 210/698

[56] References Cited

U.S. PATENT DOCUMENTS

| 4,207,285 | 6/1980 | Oppenlaender et al. ............. 422/16 |
| 4,292,162 | 9/1981 | Ambler ............................ 204/299 R |
| 4,383,937 | 5/1983 | Williams .............................. 252/392 |
| 4,411,903 | 10/1983 | Shepherd ............................. 514/315 |
| 4,450,088 | 5/1984 | Wilson et al. ....................... 252/392 |
| 4,545,942 | 10/1985 | Nagano et al. ................. 260/465 D |

FOREIGN PATENT DOCUMENTS 1149843  6/1963  Fed. Rep. of Germany.
1298670  7/1969  Fed. Rep. of Germany.
2943963  5/1981  Fed. Rep. of Germany.

OTHER PUBLICATIONS

Chemical Abstracts, 91: 211312v, vol. 91, 1979, p. 676.
Chemical Abstracts, 80: 108473x, vol. 80, 1974, p. 416.
Chemical Abstracts, 82: 43710s, vol. 82, 1975, p. 469.
Chemical Abstracts, 67: 63985d, vol. 67, 1967, p. 6003.
Chemical Abstracts, 89: 215732p and 215735s, vol. 89, 1978, p. 630.
Chemical Abstracts, 71:91863p.
Chemical Abstracts, 92:36767u.

Chemical Abstracts, 97:151229z.

Primary Examiner—Barry S. Richman
Assistant Examiner—William R. Johnson
Attorney, Agent, or Firm—Ernest G. Szoke; Henry E. Millson, Jr.

[57] ABSTRACT

Benzoyl alanines of the formula

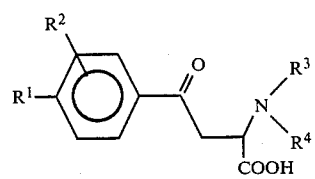

in which $R^1$ and $R^2$ can be the same or different and represent hydrogen or an alkyl radical containing from 1 to 12 carbon atoms and $R^3$ and $R^4$ can be the same or different and represent hydrogen, an unbranched or branched alkyl radical containing from 1 to 10 carbon atoms, hydroxyalkyl, alkoxyalkyl, carboxyalkyl or alkylaminoalkyl radicals containing from 1 to 3 carbon atoms in the alkyl radicals and wherein $R^3$ and $R^4$ together can be the —CH$_2$CH$_2$—O—CH$_2$CH$_2$— group or the —CH$_2$CH$_2$CH$_2$CH$_2$CH$_2$— group which form with the nitrogen atom the morpholino or the piperidino ring, respectively; with the proviso that (a) when $R^1$ is hydrogen or methyl and $R^2$ and $R^3$ are hydrogen, $R^4$ cannot represent hydroxyethyl or carboxymethyl, and (b) when $R^1$ is hydrogen or methyl and $R^2$ is hydrogen $R^3$ and $R^4$ cannot both represent hydroxyethyl, and (c) when $R^1$ and $R^2$ are both hydrogen, $R^3$ and $R^4$ together cannot be a —CH$_2$CH$_2$—O—CH$_2$CH$_2$— or a —CH$_2$CH$_2$CH$_2$CH$_2$CH$_2$— group;

and alkali metal ammonium salts thereof with ammonia, mono-, di- and triethanolamine are useful as corrosion inhibitors in aqueous solutions.

10 Claims, No Drawings

BENZOYL ALANINES AND THEIR USE AS CORROSION INHIBITORS

BACKGROUND OF THE INVENTION

1. Field of the Invention

This invention relates to benzoyl alanines and to their use as corrosion inhibitors for aqueous systems.

2. Description of Related Art

Corrosion problems arise in numerous industrial processes in which aqueous media come into contact with metal surfaces, principally with surfaces of iron, copper, aluminium, zinc or their various alloys. Examples of processes of the type in question are cleaning processes using aqueous industrial cleaner solutions, cooling processes using aqueous coolant systems and also combined cooling and lubrication in the metal-working field.

Thus, German Application No. 11 49 843 describes semiamides of maleic acid or succinic acid as additives for fuel and lubricating oils. One disadvantage of these compounds, however, lies in the fact that, in most cases, they are not soluble in water so that homogeneous dispersion throughout the process liquid cannot be guaranteed.

U.S. Pat. No. 4,207,285 also describes semiamides of maleic acid as corrosion inhibitors for aqueous systems. In this case, the alkyl groups attached to the amide nitrogen are said to contain from 9 to 12 carbon atoms. In addition, the amido acids formed are neutralized with mono-, di- or trialkanolamines or mixtures thereof.

In addition, corrosion inhibitors which have been proposed for iron in alkaline media include alkenyl succinic acids (German Application No. 29 43 963), long-chain sulfonamidocarboxylic acids (German Application No. 12 98 670), acyl sarcosinates (Winnacker-Kuechler, Chemische Technologie, C. Hanser-Verlag, Munich (1960), page 199) and alkali metal benzoates. Hitherto, fatty amines or imidazolines have mostly been used for iron in mildy acidic media, but never with entirely satisfactory results.

Alkali metal silicates or alkali metal benzoates are mostly used as corrosion inhibitors for aluminium in alkaline media, although they, too, are often unsatisfactory. One particular disadvantage of these compounds lies in the fact that they are only effective in very high concentrations.

In addition to inadequate protection against corrosion, the use of corrosion inhibitors of the above type often leads to a number of difficulties in terms of practical application. Heavy foaming of the compounds in aqueous solutions, poor solubility in water and/or poor stability to water hardness or inadquate stability in storage seriously restrict the practical application of some of the compounds mentioned. At the same time, attention also has to be directed to the often excessive toxicity of the compounds and to their extremely poor biodegradability.

DESCRIPTION OF THE INVENTION

It has now been found that aqueous systems having excellent anti-corrosion properties, high solubility in water and low foaming power are obtained when special benzoyl alanines are used as corrosion inhibitors.

Accordingly, the present invention relates to compounds corresponding to the following general formula

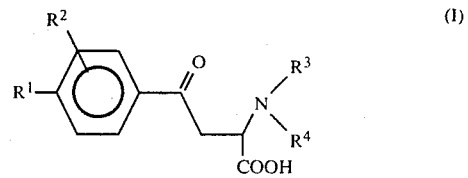

in which $R^1$ and $R^2$ can be the same or different and represent hydrogen or an alkyl radical containing from 1 to 12 carbon atoms and $R^3$ and $R^4$ can be the same or different and represent hydrogen, an unbranched or branched alkyl radical containing from 1 to 10 carbon atoms, hydroxyalkyl, alkoxyalkyl, carboxyalkyl or alkylaminoalkyl radicals containing from 1 to 3 carbon atoms in the alkyl groups thereof, and wherein $R^3$ and $R^4$ together can be the $-CH_2CH_2-O-CH_2CH_2-$ group or the $-CH_2CH_2CH_2CH_2CH_2-$ group which form with the nitrogen atom the morpholino or the piperidino ring, respectively; with the proviso that (a) when $R^1$ is hydrogen or methyl and $R^2$ and $R^3$ are hydrogen, $R^4$ cannot represent hydroxyethyl or carboxymethyl, and (b) when $R^1$ is hydrogen or methyl and $R^2$ is hydrogen, $R^3$ and $R^4$ cannot both represent hydroxyethyl, and (c) when $R^1$ and $R^2$ are both hydrogen, $R^3$ and $R^4$ together cannot be the $-CH_2CH_2-O-CH_2CH_2-$ group or the $-CH_2CH_2CH_2CH_2CH_2-$ group;

and alkali metal or ammonium salts thereof with ammonia or mono-, di- or triethanolamine.

The invention also relates to the use of compounds corresponding to formula I, in which $R^1$, $R^2$, $R^3$ and $R^4$ are as defined above but without the proviso, as corrosion inhibitors in aqueous systems.

Particularly suitable corrosion inhibitors are those compounds of formula I in which $R^1$ is an alkyl radical containing from 1 to 8 carbon atoms, preferably methyl, ethyl, propyl, i-propyl, n-butyl, tert.-butyl or n-hexyl, $R^2$ is hydrogen or a methyl radical and either $R^3$ is hydrogen and $R^4$ is hydrogen, an alkyl radical containing from 1 to 4 carbon atoms, preferably ethyl or n-butyl, a hydroxyethyl, carboxymethyl or dimethylaminopropyl radical, or $R^3$ and $R^4$ each represent a hydroxyethyl radical, or $R^3$ and $R^4$ together represent the $-CH_2CH_2-O-CH_2CH_2-$ group or the $-CH_2CH_2CH_2CH_2CH_2-$ group, i.e., including the nitrogen atom joining them they are attached to form a morpholino or piperidino ring.

The benzoyl alanines of the invention can be used as corrosion inhibitors either individually or in admixture with one another in any ratio. They develop their favorable effects in aqueous solutions, dispersions or emulsions. They are highly effective even in low concentrations, e.g., from about 0.001 to about 0.375% by weight, based on the weight of the aqueous solution. For example to protect iron surfaces against corrosion in alkali media, the corrosion inhibitor need only be used in concentrations of 0.5 kg.m$^{-3}$ to develop a high degree of activity, whereas conventional inhibitors have to be used in concentrations of from 2.5 to 10 kg.m$^{-3}$. For iron surfaces in contact with mildly acidic aqueous media, concentrations of as low as 0.1 kg.m$^{-3}$ are, surprisingly, adequate for effective protection. This is all the more surprising due to the fact that hitherto only a very few compounds which afford protection against corrosion in this pH-range have been described in the literature, i.e. the above discussed imidazolines and fatty amines. However, the protection they afford is minimal, as can be seen from the comparative test results shown in Tables 1 to 3.

It has also been found that concentrations of the above benzoyl alanines of formula I of only 0.01 kg.m$^{-3}$ provide aluminium surfaces in contact with alkaline media with optimal protection against corrosion.

In the concentrations in which they are used, the benzoyl alanines of the invention produce very little foam and show high stability to water hardness in all the waters used. This enables them to be used in aqueous systems of any composition, for example in aqueous cleaners, in lubricants, in cooling circuits, in hydraulic fluids, etc.

The benzoyl alanines of the invention are readily prepared by generally known methods. For example, they may be advantageously synthesized in high yields by the Friedel-Crafts acylation of alkylbenzenes with maleic acid anhydride, followed by the addition of amines onto the double bond of the 3-benzoyl acrylic acids obtained in the first reaction stage. The reaction conditions are those commonly used for Friedel-Crafts acylation reactions and for the addition of amines to double bonds of acrylic acids and derivatives thereof. This method of production is illustrated by the following reaction scheme:

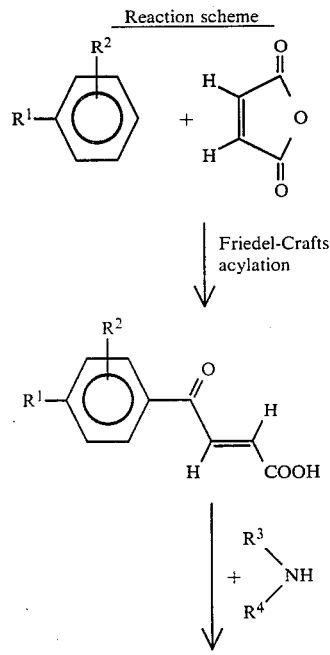

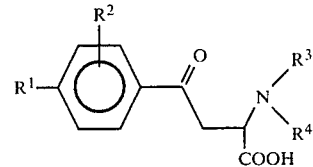

For the particular aqueous systems containing the benzoyl alanines of the invention as corrosion inhibitors, the compounds of formula I or their alkali or ammonium salts are directly dissolved in the aqueous system or are added in the form of aqueous concentrates to the particular aqueous systems.

The invention is illustrated but not limited by the following Examples.

The corrosion-inhibiting properties were determined by measuring the degree of erosion (DIN 50905/1-4) and also by the filter paper test (DIN 51360/2) DIN means German Industrial Norm.

EXAMPLE 1

Erosion test:

Three carefully pretreated and weighed strips of metal (unalloyed steel, 80×15×1 mm) were suspended in a 1 liter vessel containing 800 ml of test water, 50 ml of buffer solution and a predetermined quantity of a benzoyl alanine of the invention (formula I) and left therein for 3 hours at room temperature. The solution was stirred at a speed of 80 r.p.m.$^{-1}$.

The test water used as the corrosive medium was prepared in accordance with DIN 51360/2 and buffered to pH 9.0 with ammonia/ammonium chloride.

At the end of the test period, the metal strips were dried and weighed. The corrosion inhibition value S, based on a blank test specimen, was calculated from the weight loss:

$$S = 100(1 - a/b)$$

a = weight loss of the test specimen
b = weight loss of the blank test specimen

The results of the erosion test are shown in Table 1.

TABLE 1

| $R^1$ | $R^2$ | $R^3$ | $R^4$ | Base | Corrosion inhibition value S | | |
|---|---|---|---|---|---|---|---|
| | | | | | $0.25^a$ | $0.1^a$ | $0.05^a$ |
| $CH_3$ | $CH_3$ | H | $-CH_2CH_2OH$ | $NH_3$ | 95 | 94 | 30 |
| $(CH_3)_2CH$ | H | H | " | " | 99 | 95 | 95 |
| " | " | " | " | $DEA^b$ | 96 | 90 | 42 |
| $(CH_3)_3C$ | " | " | " | $NH_3$ | 99 | 99 | 90 |
| " | " | " | " | $MEA^c$ | 97 | 96 | 66 |
| $n-C_6H_{13}$ | " | " | $-(CH_2)_3N(CH_3)_2$ | $NH_3$ | 92 | 91 | 85 |
| $CH_3$ | " | " | $-(CH_2)_3CH_3$ | " | 94 | 64 | 40 |
| $CH_2CH_3$ | " | " | " | " | 99 | 98 | 89 |
| $CH_3$ | $CH_3$ | " | " | " | 91 | 81 | 30 |
| Na—benzoate (Comparison) | | | | | 52 | 18 | 0 |

TABLE 1-continued

| R¹ | R² | R³ | R⁴ | Base | Corrosion inhibition value S | | |
|---|---|---|---|---|---|---|---|
| | | | | | 0.25ᵃ | 0.1ᵃ | 0.05ᵃ |
| Maleic acid mono-2-ethylhexylamide (Comparison) | | | | | 69 | 0 | 0 |
| Benzene sulfonamidocaproic acid (Comparison) | | | | | 65 | 0 | 0 |

ᵃInhibitor concentration in % by weight
ᵇDEA = diethanolamine
ᶜMEA = monoethanolamine

EXAMPLE 2

Gray iron filter paper test:
The gray iron filter paper test was carried out in accordance with DIN 51360/2. The test medium used was DIN water having a hardness of 20° d (d=German hardness). The claimed compounds were tested in the form of their diethanolamine salts (pH 9.7).

Evaluation was carried out in degrees of corrosion in accordance with the above DIN Standard:
0 = no corrosion
1 = traces of corrosion
2 = slight corrosion
3 = moderate corrosion
4 = serious corrosion The test results are shown in Table 2.

TABLE 2

| R¹ | R² | R³ | R⁴ | Degree of corrosion | | |
|---|---|---|---|---|---|---|
| | | | | 0.375ᵃ | 0.250ᵃ | 0.125ᵃ |
| Me | Me | H | CH₂CH₂OH | 0 | 0 | 1 |
| " | H | " | " | 0 | 1 | 2 |
| Me₂CH | " | " | " | 0 | 0 | 2 |
| ME₃C | " | " | (CH₂)₃N(CH₃)₂ | 0 | 1 | 2 |
| n-C₆H₁₃ | " | " | " | 0 | 0 | 2 |
| Me | Me | " | (CH₂)₃CH₃ | 0 | 0 | 2 |
| Me | H | " | " | 0 | 0 | 2 |
| Et | " | " | " | 0 | 0 | 1 |
| n-C₄H₉ | " | CH₂CH₂OH | CH₂CH₂OH | 0 | 0 | 1 |
| CH₃ | " | H | CH₂CH₃ | 0 | 0 | 3 |
| (CH₃)₂CH | " | " | CH₂COOH | 0 | 1 | 3 |
| " | " | —CH₂CH₂OCH₂CH₂— | | 0 | 1 | 2 |
| Comparison: | | | | | | |
| Caprylic acid | | | | 3 | 3 | 4 |
| Maleic acid mono-2-ethylhexylamide | | | | 0 | 1 | 3 |
| Benzene sulfonamidocaproic acid | | | | 1 | 1 | 3 |

ᵃInhibitor concentration in % by weight

EXAMPLE 3

The procedure was as in Example 1, the test medium being buffered to pH 4 with HOAc/NaOAc. The corrosion inhibition values are shown in Table 3.

TABLE 3

| R¹ | R² | R³ | R⁴ | Corrosion inhibition value S | | |
|---|---|---|---|---|---|---|
| | | | | 0.05ᵃ | 0.025ᵃ | 0.01ᵃ |
| (CH₃)₂CH | H | H | (CH₂)₃N(CH₃)₂ | 91 | 81 | 65 |
| (CH₃)₃C | " | " | " | 92 | 91 | 87 |
| Comparison 1ᵇ | | | | 34 | 28 | 27 |
| Comparison 2ᶜ | | | | 33 | 29 | 28 |

ᵃInhibitor concentration in % by weight
ᵇComparison 1 = 1-(2'-hydroxyethyl)-2-oleyl imidazoline
ᶜComparison 2 = 1-(2'-aminoethyl)-2-oleyl imidazoline

EXAMPLE 4

The procedure was as in Example 1 using aluminum strips measuring 80×15×1 mm. Test period: 65 h. The claimed compounds were tested in the form of their sodium salts. The corrosion inhibition values are shown in Table 4.

TABLE 4

| R¹ | R² | R³ | R⁴ | Corrosion inhibition value S | | |
|---|---|---|---|---|---|---|
| | | | | 0.05ᵃ | 0.025ᵃ | 0.01ᵃ |
| (CH₃)₂CH | H | H | CH₂CH₂OH | 96 | 28 | 22 |
| (CH₃)₃C | " | " | " | 99 | 45 | 32 |
| n-C₆H₁₃ | " | " | " | 99 | 99 | 99 |
| " | " | " | (CH₂)₃N(CH₃)₂ | 99 | 99 | 28 |

ᵃInhibitor concentration in % by weight
Comparison: In these concentrations, Na—benzoate does not afford any protection against corrosion.

What is claimed is:
1. A method for preventing corrosion of metals from contact with an aqueous solution comprising adding to said aqueous solution a corrosion-inhibiting quantity of at least one benzoyl alanine of the formula

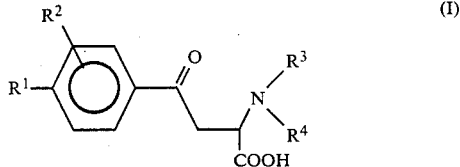

(I)

wherein R¹ and R² can be the same or different and represent hydrogen or an alkyl radical containing from 1 to 12 carbon atoms and R³ and R⁴ can be the same or different and represent hydrogen, an unbranched or branched alkyl radical containing from 1 to 10 carbon atoms, hydroxyalkyl, alkoxyalkyl, carboxyalkyl or alkylaminoalkyl radicals containing from 1 to 3 carbon atoms in the alkyl groups thereof, and wherein R³ and R⁴ together can be the —CH₂CH₂—O—CH₂CH₂— group or the —CH₂CH₂CH₂CH₂CH₂— group which form with the nitrogen atom the morpholino or the piperidino ring, or an alkali metal or an ammonium salt of the above benzoyl alanine with a base from the group consisting of ammonia, mono-, di- or triethanolamine.

2. The method of claim 1 wherein about 0.001–0.375% by weight of said at least one benzoyl alanine is added to said aqueous solution, based upon the total weight of said solution.

3. The method of claim 1 wherein the substituted combination is of at least one of:

|     | $R^1$ is:        | $R^2$ is:       | $R^3$ is: | $R^4$ is:            | the base is: |
| --- | ---------------- | --------------- | --------- | -------------------- | ------------ |
| (a) | $CH_3$           | $CH_3$          | H         | $-CH_2CH_2OH$        | $NH_3$;      |
| (b) | $(CH_3)_2CH$     | H               | H         | $-CH_2CH_2OH$        | $NH_3$;      |
| (c) | $(CH_3)_2CH$     | H               | H         | $-CH_2CH_2OH$        | DEA;         |
| (d) | $(CH_3)_3C$      | H               | H         | $-CH_2CH_2OH$        | $NH_3$;      |
| (e) | $(CH_3)_3C$      | H               | H         | $-CH_2CH_2OH$        | DEA;         |
| (f) | $n-C_6H_{13}$    | H               | H         | $(CH_2)_3N(CH_3)_2$  | $NH_3$;      |
| (g) | $CH_3$           | H               | H         | $-(CH_2)_3CH_3$      | $NH_3$;      |
| (h) | $CH_2CH_3$       | H               | H         | $-(CH_2)_3CH_3$      | $NH_3$;      |
| (i) | $CH_3$           | $CH_3$          | H         | $-(CH_2)_3CH_3$      | $NH_3$;      |
| (j) | $CH_3$           | $CH_3$          | H         | $CH_2CH_2OH$         | DEA;         |
| (k) | $CH_3$           | H               | H         | $CH_2CH_2OH$         | DEA;         |
| (l) | $(CH_3)_3C$      | H               | H         | $(CH_2)_3N(CH_3)_2$  | DEA;         |
| (m) | $n-C_6H_{13}$    | H               | H         | $(CH_2)_3N(CH_3)_2$  | DEA;         |
| (n) | $CH_3$           | $CH_3$          | H         | $-(CH_2)_3CH_3$      | DEA;         |
| (o) | $CH_3$           | H               | H         | $-(CH_2)_3CH_3$      | DEA;         |
| (p) | $CH_2CH_3$       | H               | H         | $-(CH_2)_3CH_3$      | DEA;         |
| (q) | $n-C_4H_9$       | H               | H         | $CH_2CH_2OH$         | DEA;         |
| (r) | $CH_3$           | H               | H         | $CH_2CH_3$           | DEA;         |
| (s) | $(CH_3)_2CH$     | H               | H         | $CH_2COOH$           | DEA;         |
| (t) | $(CH_3)_2CH$     | H               | $-CH_2CH_2OCH_2CH_2-$ |                 | DEA;         |
| (u) | $(CH_3)_2CH$     | H               | H         | $(CH_2)_3N(CH_3)_2$  | —;           |
| (v) | $(CH_3)_2CH$     | H               | H         | $CH_2CH_2OH$         | Na salt;     |
| (w) | $(CH_3)_3C$      | H               | H         | $CH_2CH_2OH$         | Na salt;     |
| (x) | $n-C_6H_{13}$    | H               | H         | $CH_2CH_2OH$         | Na salt; or  |
| (y) | $n-C_6H_{13}$    | H               | H         | $(CH_2)_3N(CH_3)_2$  | Na salt.     |

4. The method of claim 3 wherein about 0.001–0.375% by weight of said at least one benzoyl alanine is added to said aqueous solution, based upon the total weight of said solution.

5. The method of claim 1 wherein $R^1$ is a $C_1$–$C_8$ alkyl group, $R^2$ is hydrogen or methyl, $R^3$ is hydrogen, and $R^4$ is hydrogen, a $C_1$–$C_4$ alkyl group, hydroxyethyl, carboxymethyl, or dimethylaminopropyl, or $R^3$ and $R^4$ are both hydroxyethyl, or $R^3$ and $R^4$ together are $-CH_2CH_2OCH_2CH_2-$ or $-CH_2CH_2CH_2CH_2CH_2-$.

6. The method of claim 5 wherein about 0.001–0.375% by weight of said at least one benzoyl alanine is added to said aqueous solution, based upon the total weight of said solution.

7. The method of claim 5 wherein $R^1$ is methyl, ethyl, propyl, isopropyl, n-butyl, tert-butyl, or n-hexyl.

8. The method of claim 7 wherein about 0.001–0.375% by weight of said at least one benzoyl alanine is added to said aqueous solution, based upon the total weight of said solution.

9. The method of claim 5 wherein $R^3$ is hydrogen and $R^4$ is ethyl or n-butyl.

10. The method of claim 9 wherein about 0.001–0.375% by weight of said at least one benzoyl alanine is added to said aqueous solution, based upon the total weight of said solution.

* * * * *